US012257017B2

United States Patent
Daley, II et al.

(10) Patent No.: US 12,257,017 B2
(45) Date of Patent: *Mar. 25, 2025

(54) IMAGING SYSTEM GANTRY AND PATIENT DRAPE

(71) Applicant: InSurgery, LLC, Lunenburg, MA (US)

(72) Inventors: Edward J. Daley, II, Maynard, MA (US); Russell Stanton, Lunenburg, MA (US)

(73) Assignee: InSurgery, LLC, Lunenburg, MA (US)

( * ) Notice: Subject to any disclaimer, the term of this patent is extended or adjusted under 35 U.S.C. 154(b) by 828 days.

This patent is subject to a terminal disclaimer.

(21) Appl. No.: 17/353,010

(22) Filed: Jun. 21, 2021

(65) Prior Publication Data

US 2021/0401529 A1  Dec. 30, 2021

Related U.S. Application Data

(60) Provisional application No. 63/044,490, filed on Jun. 26, 2020.

(51) Int. Cl.
*A61B 46/10* (2016.01)
*A61B 6/00* (2006.01)
*A61B 6/03* (2006.01)

(52) U.S. Cl.
CPC .............. *A61B 46/10* (2016.02); *A61B 6/032* (2013.01); *A61B 6/4447* (2013.01)

(58) Field of Classification Search
CPC ......... A61B 46/00; A61B 46/10; A61B 46/20; A61B 6/032; A61B 6/4447
See application file for complete search history.

(56) References Cited

U.S. PATENT DOCUMENTS

| 6,456,684 | B1 * | 9/2002 | Mun .................... A61B 6/102 |
| | | | 5/601 |
| 6,694,981 | B2 | 2/2004 | Gingles et al. |
| 6,843,252 | B2 | 1/2005 | Harrison et al. |
| 8,770,839 | B2 | 7/2014 | Gregerson et al. |
| 8,807,138 | B2 * | 8/2014 | Byers ................ A61N 5/1077 |
| | | | 128/853 |
| 11,877,876 | B2 * | 1/2024 | Daley, II .............. A61B 6/547 |
| 2006/0124138 | A1 | 6/2006 | Dusenbery et al. |
| 2011/0281064 | A1 | 11/2011 | Murphy et al. |

(Continued)

FOREIGN PATENT DOCUMENTS

| DE | 102010040956 A1 * | 3/2012 | ............ A61B 46/10 |
| WO | 2018071720 A1 | 4/2018 | |
| WO | 2018171720 A1 | 9/2018 | |

OTHER PUBLICATIONS

Written Opinion of International Application No. PCT/US2021/038358 date of mailing Sep. 30, 2021, five (5) pages.

*Primary Examiner* — Keri J Nelson
(74) *Attorney, Agent, or Firm* — Iandiorio Teska & Coleman, LLP

(57) ABSTRACT

An imaging system gantry and patient drape includes a gantry first outer sidewall covering portion biased into a deployed shape and collapsible, a gantry inner wall covering portion extending inward of the gantry first outer sidewall covering portion, and a patient envelope portion. One or more retainers secure a portion of the drape to the gantry. In some versions, one or more drape portions rotate with the gantry and one or more other drape portions do not rotate with the gantry.

19 Claims, 18 Drawing Sheets

(56) References Cited

U.S. PATENT DOCUMENTS

| | | |
|---|---|---|
| 2014/0318551 A1 | 10/2014 | Contour |
| 2014/0373851 A1 | 12/2014 | Powley et al. |
| 2015/0065839 A1 | 3/2015 | Farah et al. |
| 2015/0173836 A1 | 6/2015 | Pack et al. |
| 2020/0054299 A1 | 2/2020 | Daley, II et al. |

* cited by examiner

IMAGING SYSTEM GANTRY AND PATIENT DRAPE

RELATED APPLICATIONS

This application claims benefit of and priority to U.S. Provisional Application Ser. No. 63/044,490 filed Jun. 26, 2020, under 35 U.S.C. §§ 119, 120, 363, 365, and 37 C.F.R. § 1.55 and § 1.78, and which is incorporated herein by this reference.

FIELD OF THE INVENTION

This subject invention relates to medical drapes.

BACKGROUND OF THE INVENTION

Imaging systems such as computerized tomography (CT) machines are often used during surgery. A typical CT machine includes an O-shaped gantry with a patient channel therethrough mounted to a gimbal itself mounted to a base. The gimbal can be moved linearly relative to the base. The base may also include a column supporting a patient table which can be moved linearly with respect to the column in and out of the gantry patient channel. See, for example, U.S. Pat. No. 8,770,839 incorporated herein by this reference. Other imaging systems include the Medtronic O-Arm and systems from Siemens, Philips, and Brain Lab. Some imaging systems include C-arms and other shapes for the imaging source and detector.

Sterility, of course, is extremely important in the operating theater. If a physician or nurse even touches a non-sterile surface or item, the health care professional must then leave the operating room, rescrub, and don new operating room attire. The CT gantry is considered non-sterile. Breaking sterility can result in increased time and cost associated with surgery.

Accordingly, sterile drapes for imaging machines have been developed. For example, U.S. Published Patent Application No. 2011/0281064 (incorporated herein by this reference) discloses a drape for the patient channel of an imaging machine. The drape is in a form of a sleeve with elastic bands about each opening which are stretched over lips at the patient channel openings of the machine. See also WO2018/0171720 incorporated herein by this reference.

There are also patient drapes. See for example U.S. Publication Nos. 2014/0373851; 2015/0065839; 2006/0124138; and 2014/0318551; and U.S. Pat. No. 6,694,981.

In some operations, both the patient and the imaging device are draped. In one example, a patient subjected to a cranial procedure such as a craniotomy (or deep brain stimulation procedure) lies in the patient channel of the imaging machine and a drape material extends from the imaging machine and is secured to the patient's head via a sterile adhesive patch (e.g., the Ioban drape available from 3M).

BRIEF SUMMARY OF THE INVENTION

It can be difficult and time consuming to deploy drapes without breaking sterility. Featured is a new drape which is fast and easy to deploy, fast and easy to remove, and which can be manufactured inexpensively.

Featured is an imaging system gantry and patient drape comprising a gantry first outer sidewall covering portion biased into a deployed shape and collapsible. A gantry inner wall covering portion extends inward of the gantry first outer sidewall covering portion. Further included is a patient envelope portion and one or more retainers securing a portion of the drape to the gantry.

Preferably, the patient envelope portion extends from the gantry inner wall covering portion outwardly through the gantry. The patient envelope portion may include a patient fenestration located at a terminal portion of the patient envelope portion. The patient envelope portion may include a stiffener forming a patient viewing window. The gantry first outer sidewall covering portion preferably includes a flexible spring member.

In one version, one portion of the drape rotates relative to another portion of the drape. For example, the one or more retainers rotate relative to the gantry first outer sidewall covering portion, the gantry inner wall covering portion and the patient envelope portion. In one version, the one or more retainers include a channel for the flexible spring member and the channel includes a roller for the flexible spring member. In another version, one drape portion includes a track and the other drape portion includes a rail received in said track. For example, a first ring is secured to one drape portion and a second ring is secured to other drape portion, the first ring including the track and the second ring including the rail. The first ring can be secured to a terminal portion of the patent envelope portion and the second ring can be secured to the patent envelope portion.

The one or more retainers preferably include a plurality of stays connectable to the gantry. For example, the one or more stays may extend from the gantry inner wall covering portion for securing to a gantry second outer sidewall. The drape may further include retainers associated with the gantry first outer sidewall covering portion for attachment to the gantry.

Also featured is an imaging system gantry and patient drape. A gantry first outer sidewall covering portion is biased into a deployed shape and collapsible via a flexible spring member. A gantry inner wall covering portion extends inward of the gantry first outer sidewall covering portion. The drape also includes a patient envelope portion. One or more retainers secure a portion of the drape to the gantry. One or more first drape portions rotate with the gantry and one or more second drape portions are stationary with respect to rotation of the gantry.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
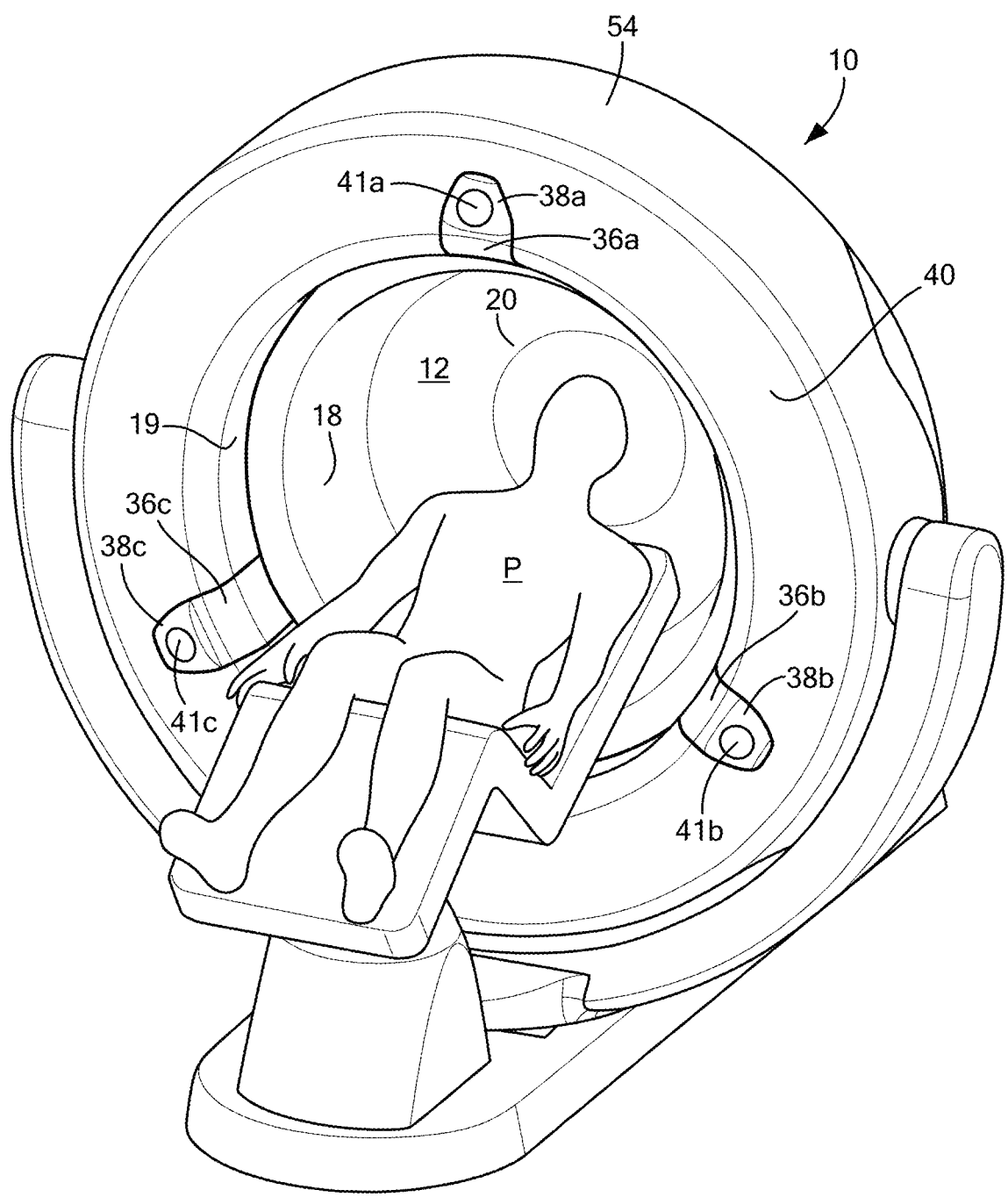
FIG. 1 is a schematic view showing an example of a drape for one style CT machine with O-shaped gantry showing the patient side of the drape.
Figure 2:
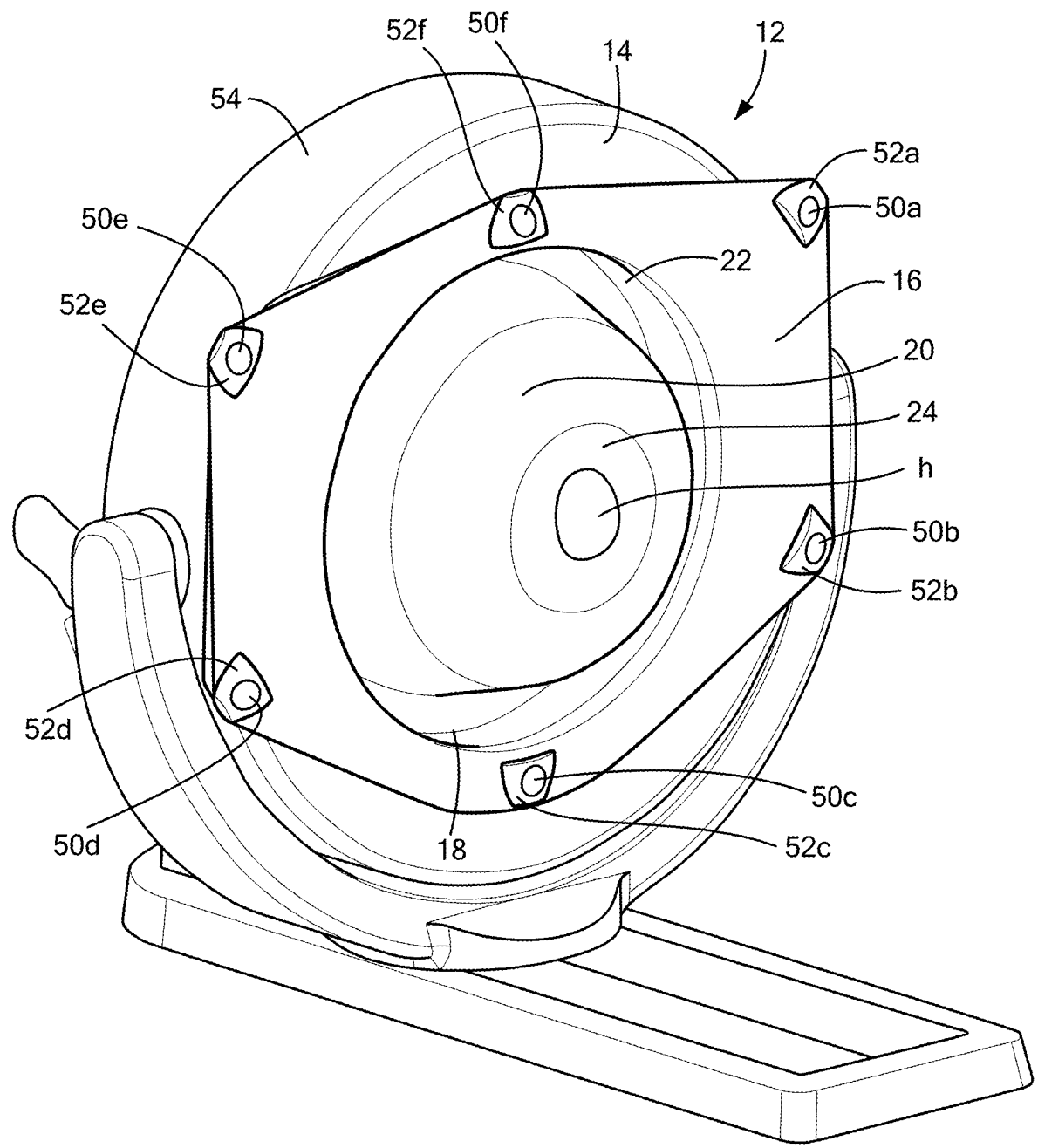
FIG. 2 is a schematic view showing the other side of the drape of FIG. 1.
Figure 3:
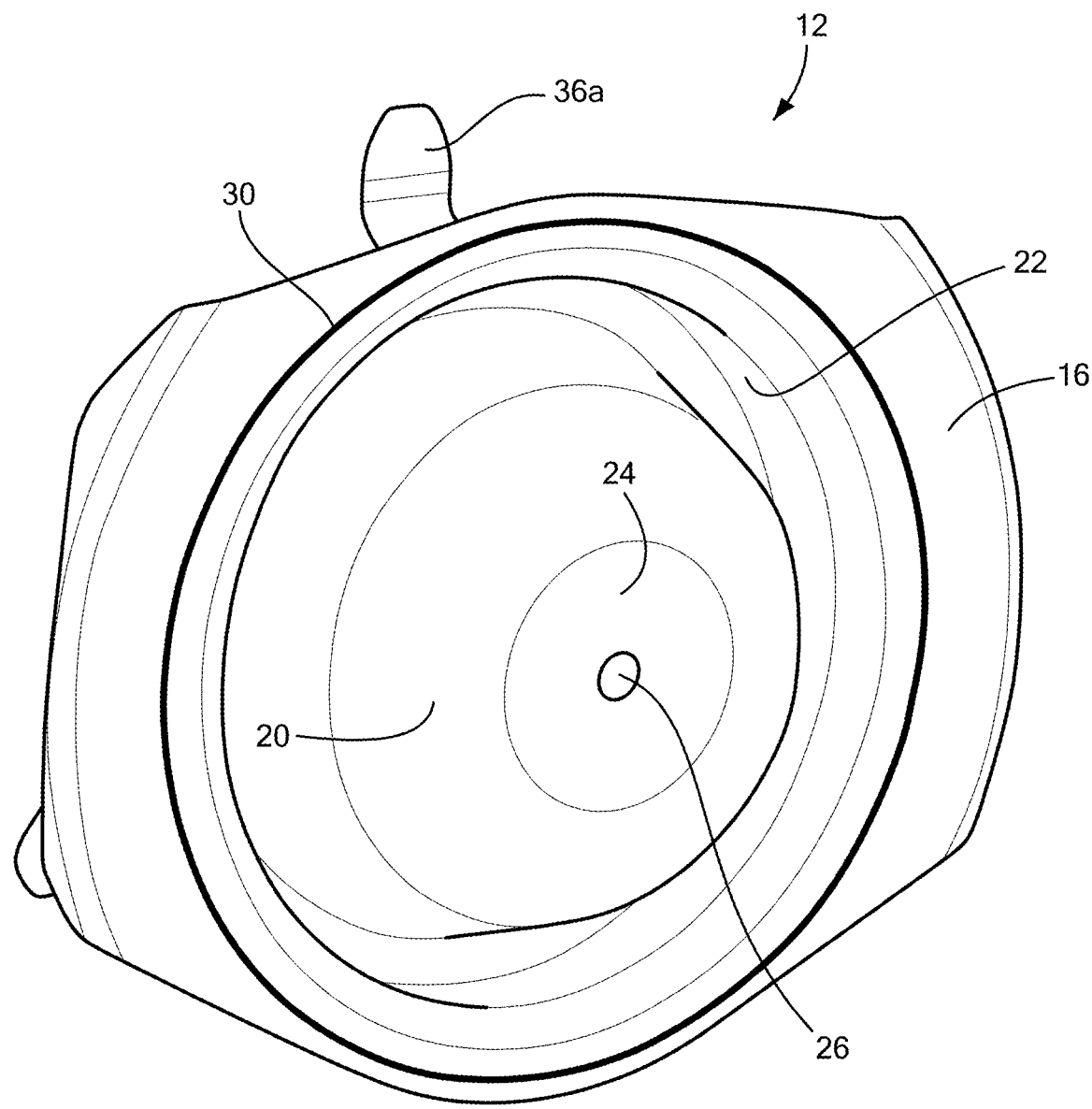
FIG. 3 is another schematic view showing an example of a drape.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIGS. 1-4 show patient P positioned within imaging system gantry 10 for a cranial procedure. Drape 12 is also shown. In this example, imaging system gantry 10 is 0-shaped but the drape can be deployed on C- and other shaped gantries.

Drape 12 in this example includes gantry first outer sidewall covering portion 16 which may cover all or only some of gantry sidewall 14. Gantry inner wall covering portion 18 extends inward of portion 16 to cover all or a portion the patient channel inner circular wall 19. Patient envelope portion 20 preferably extends from the gantry inner wall covering portion 18 inner edge 22 outwardly through the gantry as shown. The terminal portion 24 of the patient envelope portion may include fenestration 26 for the patient's head h (or some other body part). In other examples, there is no fenestration but the surgeon may create one by cutting the drape after deployment of the drape. In some cases, another drape such as an Ioban drape may be secured to both the patient's head h and to the terminal portion 24 of the patient envelope portion 20. In other examples, the fenestration in the drape is formed such that it securely attaches about the patient's head.

Gantry first outer sidewall covering portion 16 is preferably biased into a deployed (e.g., round) shape and yet is also collapsible for compact shipping and storage, for example, in a sterile package. In one example, the gantry first outer sidewall covering portion 16 includes a peripheral flexible spring member 30, FIG. 4. For example, a spring band may be attached at or near the outer periphery of covering portion 16 or resides in a sleeve or channel at or near the periphery of the covering portion. The spring band is preferably flexible in order to package the drape but also has a memory automatically urging the spring band back into a preferably hoop like shape when released from the packaging. Various shape memory alloys are known in the art. The drape thus preferably self-deploys. The spring member(s) can be made of metal or non-metal (e.g., for magnetic resonance applications). And, in some cases, as noted below, the drape may employ secondary fixation devise such as adhesive, hook and loop fasteners, hooks, male/female connectors, docks, static cling, or the like to better secure the drape to the gantry. The drape may be made of a plastic sheeting, for example low-density polyethylene.

There are typically one or more retainers securing one or more drape portions to the gantry. In the example shown, stays 36a, 36b, and 36c each with a respective outer hand sleeve 38a, 38b, and 38c extend from gantry inner wall covering portion 18 and are securable to the gantry second outer sidewall 40. Each stay may include a hook and loop fasteners patch 41a, 41b, and 41c, respectively, for releasably mating with a respective hook and loop fasteners patch on sidewall 40. Gantry first outer sidewall covering portion 16, FIG. 2 may also include retainers including hook and loop fasteners patches 50a-50f each with a hand sleeve 52a-52f, respectively. The hook and loop fasteners patch is releasably mated with corresponding hook and loop fasteners patches on the gantry first outer sidewall 14 and/or gantry outer face 54.

Figure 4:
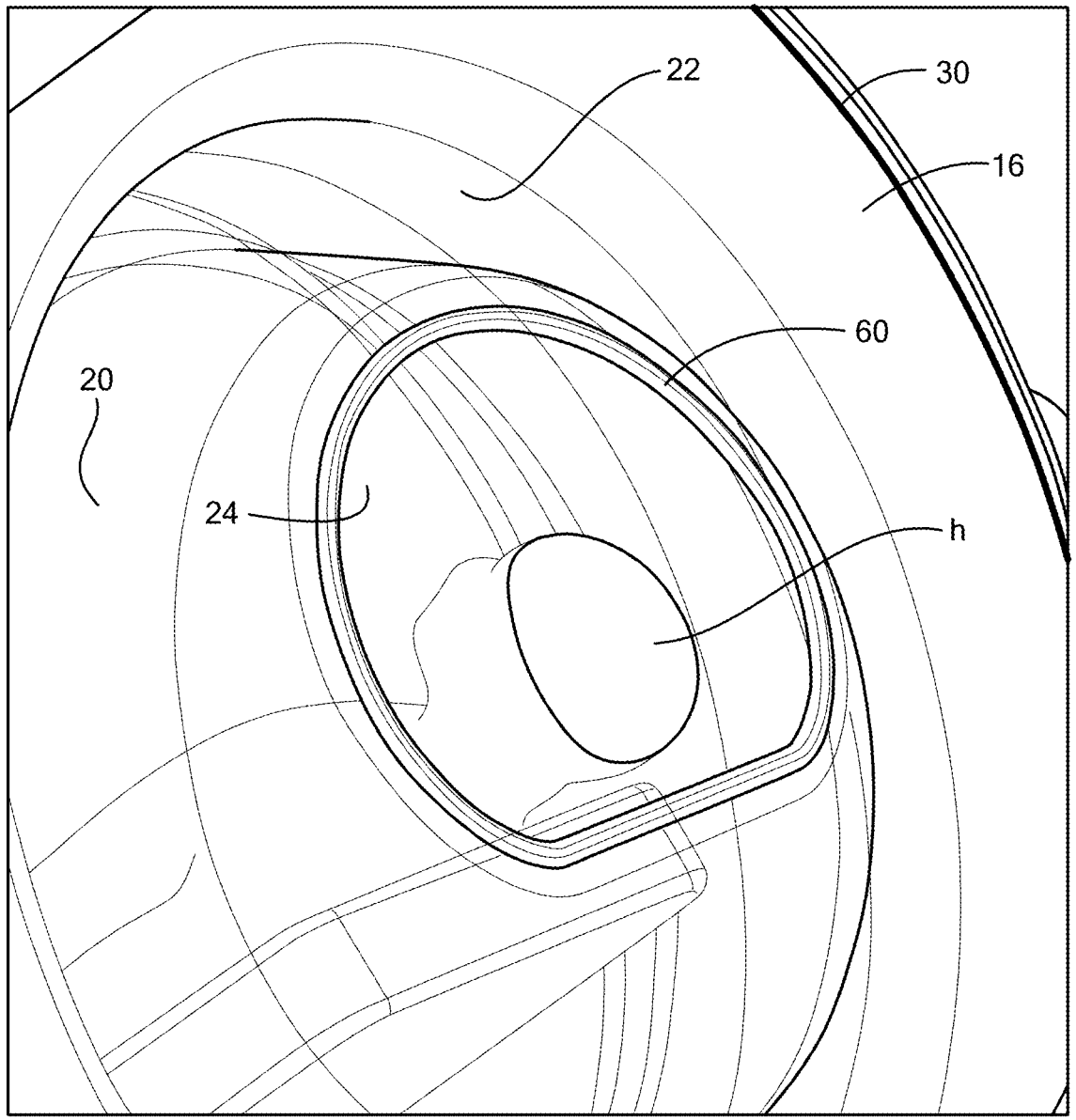
FIG. 4 is a schematic view showing a version of a drape with a patient window portion.

In some embodiments, as shown in FIG. 4, the terminal portion 24 of patient envelope portion 20 may include stiffener 60 forming a patient viewing window. Stiffener 60 is secured to terminal portion 24 as shown and be made of radiolucent plastic material. The stiffener when integrated into the drape acts like a brim and keeps the drape from obscuring the patient's face. Patients are often awake during some procedures and may at times feel smothered by extra drape material. Also, the anesthesiologists or other physician is now provided a clear view of the patient's face.

Figure 5:
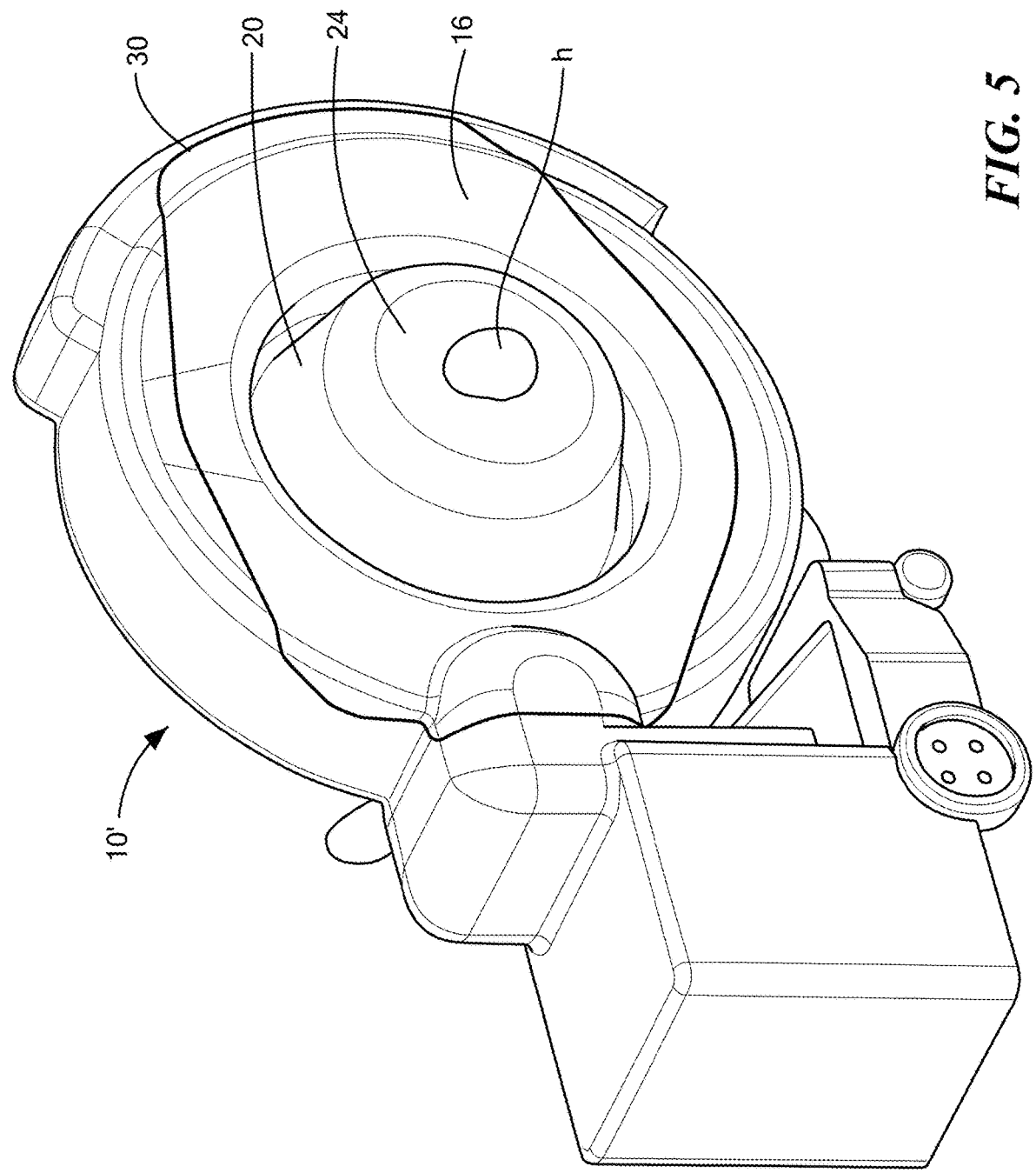
FIGS. 5-6 are schematic views showing another example of a drape for a different style CT machine O-shaped gantry.
Figure 6:
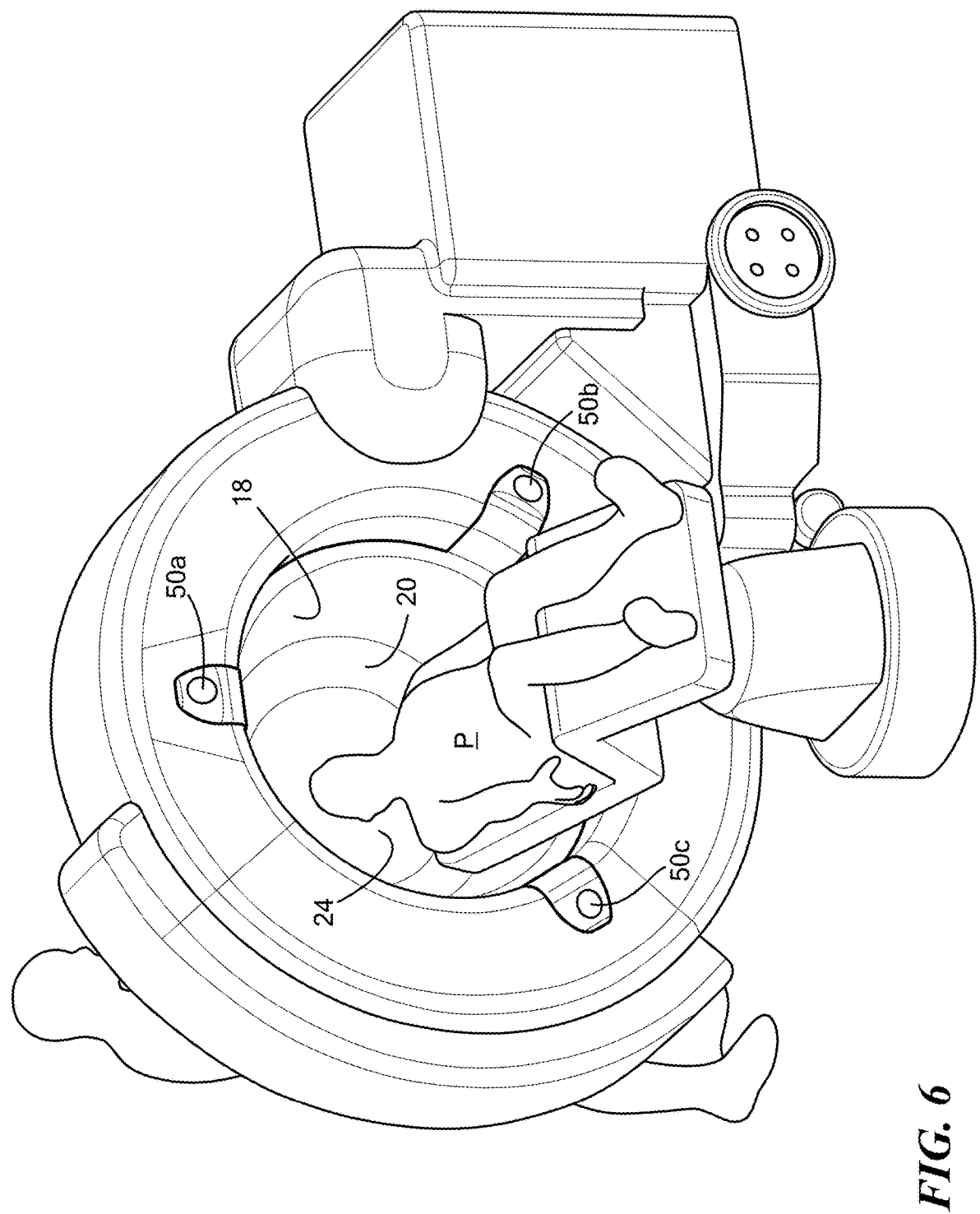
Figure 7:
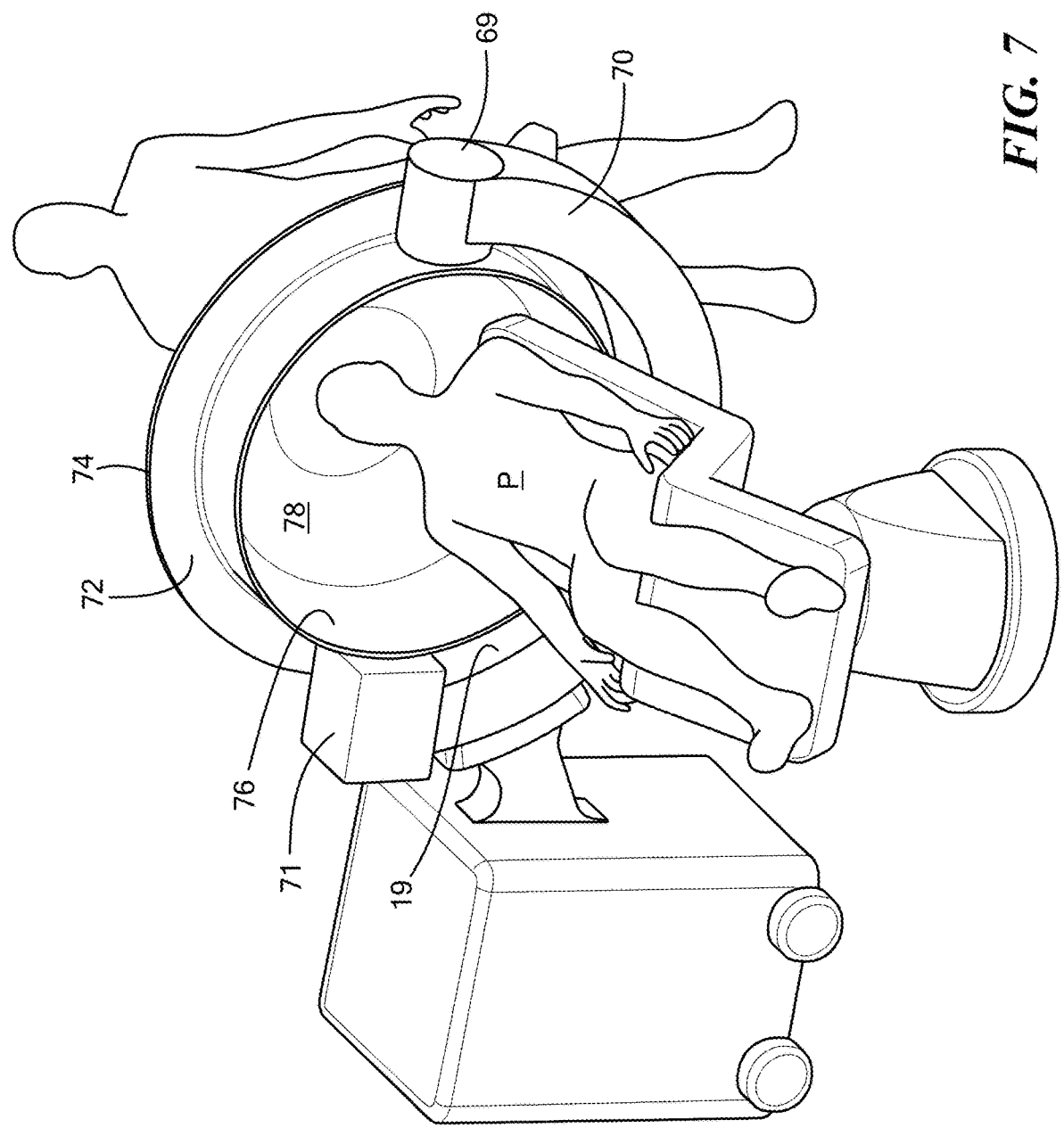
FIG. 7 is a schematic view showing the patient side of a drape for a C-shaped gantry.

FIGS. 5-6 show a drape for a different style gantry 10'.

FIGS. 7-20 show a version of a patient/gantry drape for an imaging system with a C-arm 70 and imager 69 and detector 71 mounted thereon. Gantry first outer sidewall covering portion 72 is biased into a deployed round shape preferably by rim located spring member 74. Gantry inner wall covering portion 76 extends inward of gantry portion 72. Patient envelope portion 78 is also shown. Retainers in the forms of stays 80a, 80b each with a hook and loop fasteners portion 82a, 82b and sleeves 84a, 84b are releasably attached to gantry outer sidewalls 86.

Because patient envelope portion 78 is usually fixed to the patient and because the lower portion 72 of the C-arm gantry is not considered sterile, it is preferable that if the gantry 70 rotates, then drape portions 72, 76 and 78 do not. Thus, the drape may include portions which do rotate with the gantry and portions which do not.

Figure 8:
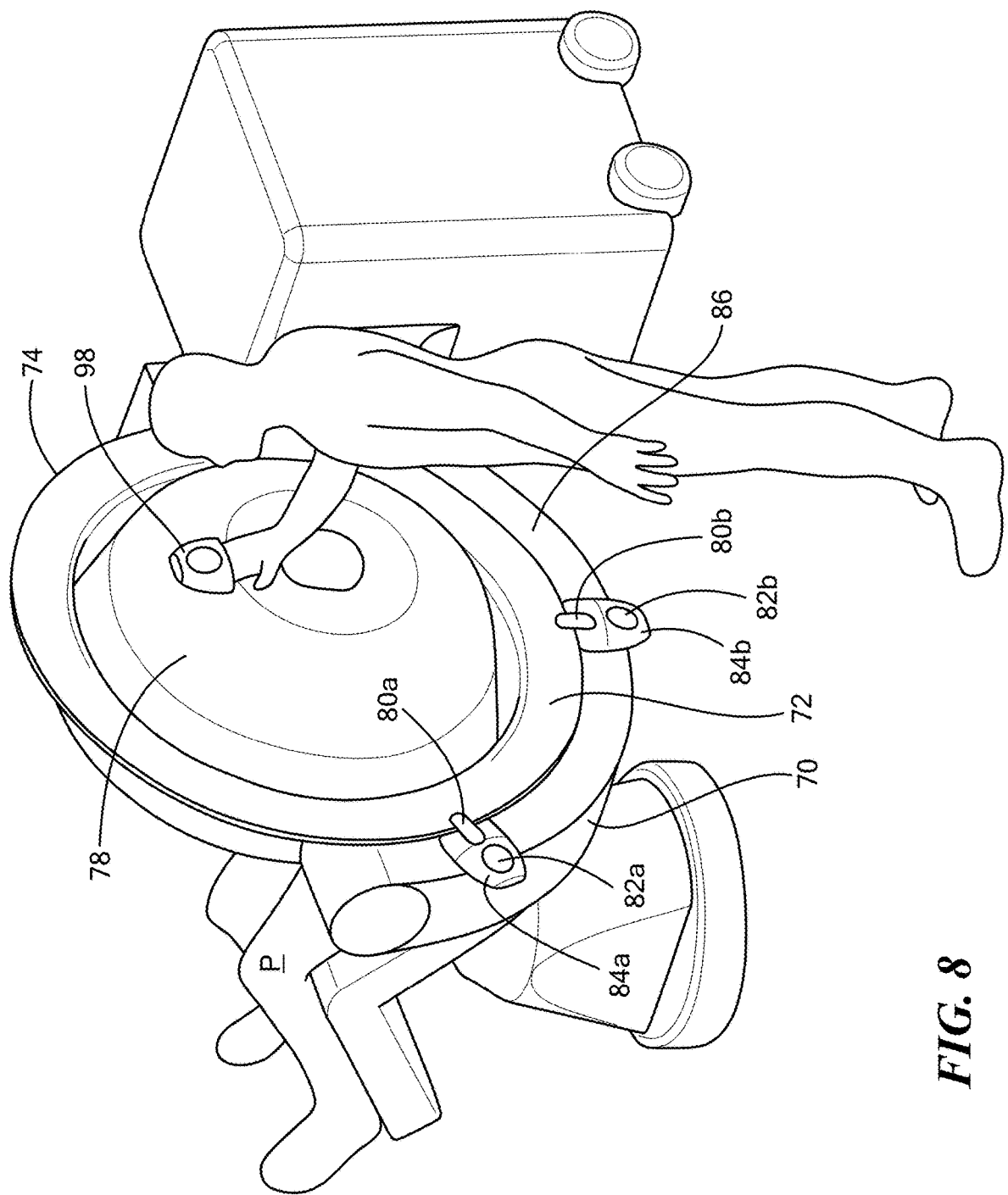
FIG. 8 is a schematic view showing the other side of the drape of FIG. 7.
Figure 9:
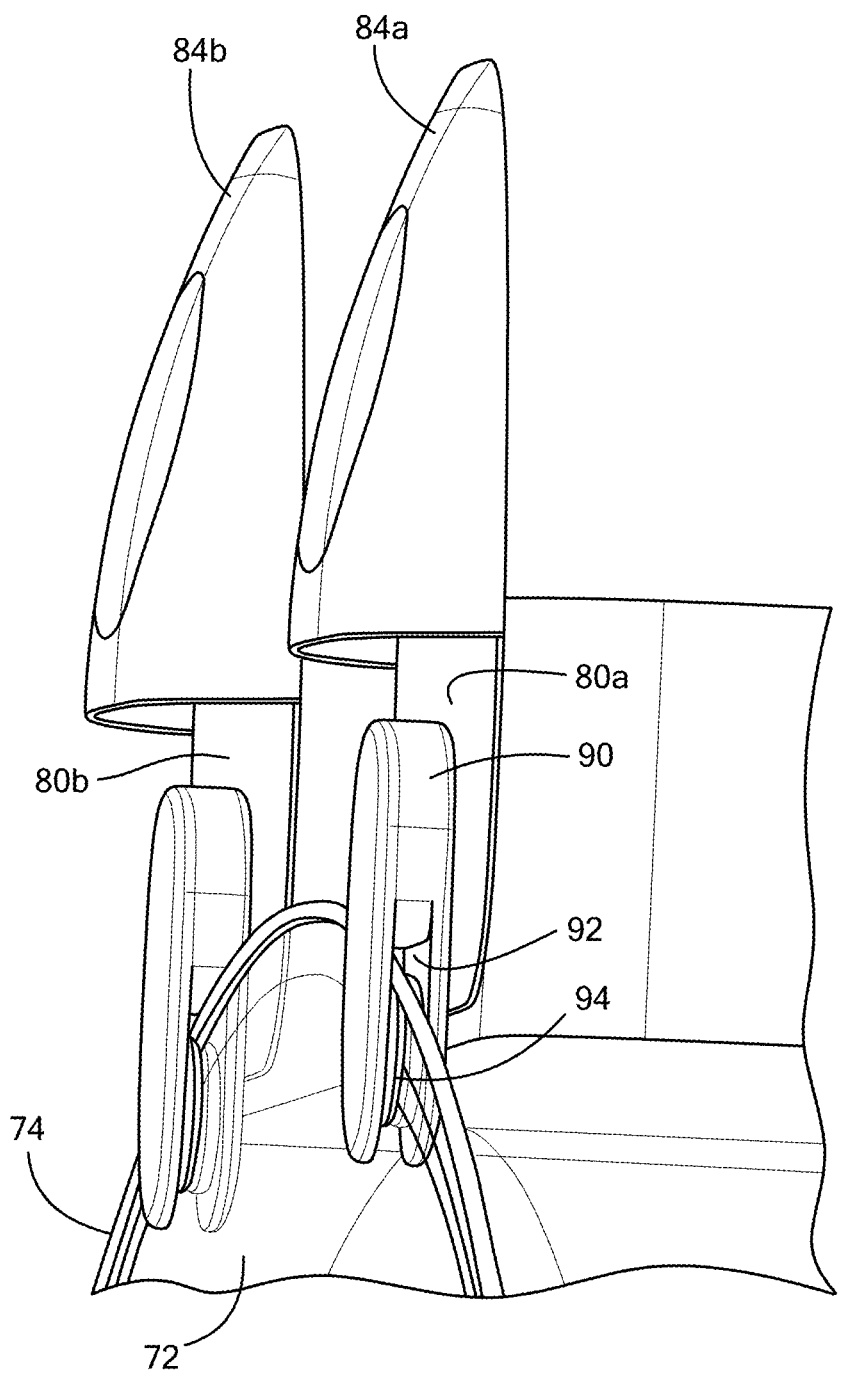
FIG. 9 is a schematic view showing an example of how the drape can rotate relative to drape retainers.
Figure 10:
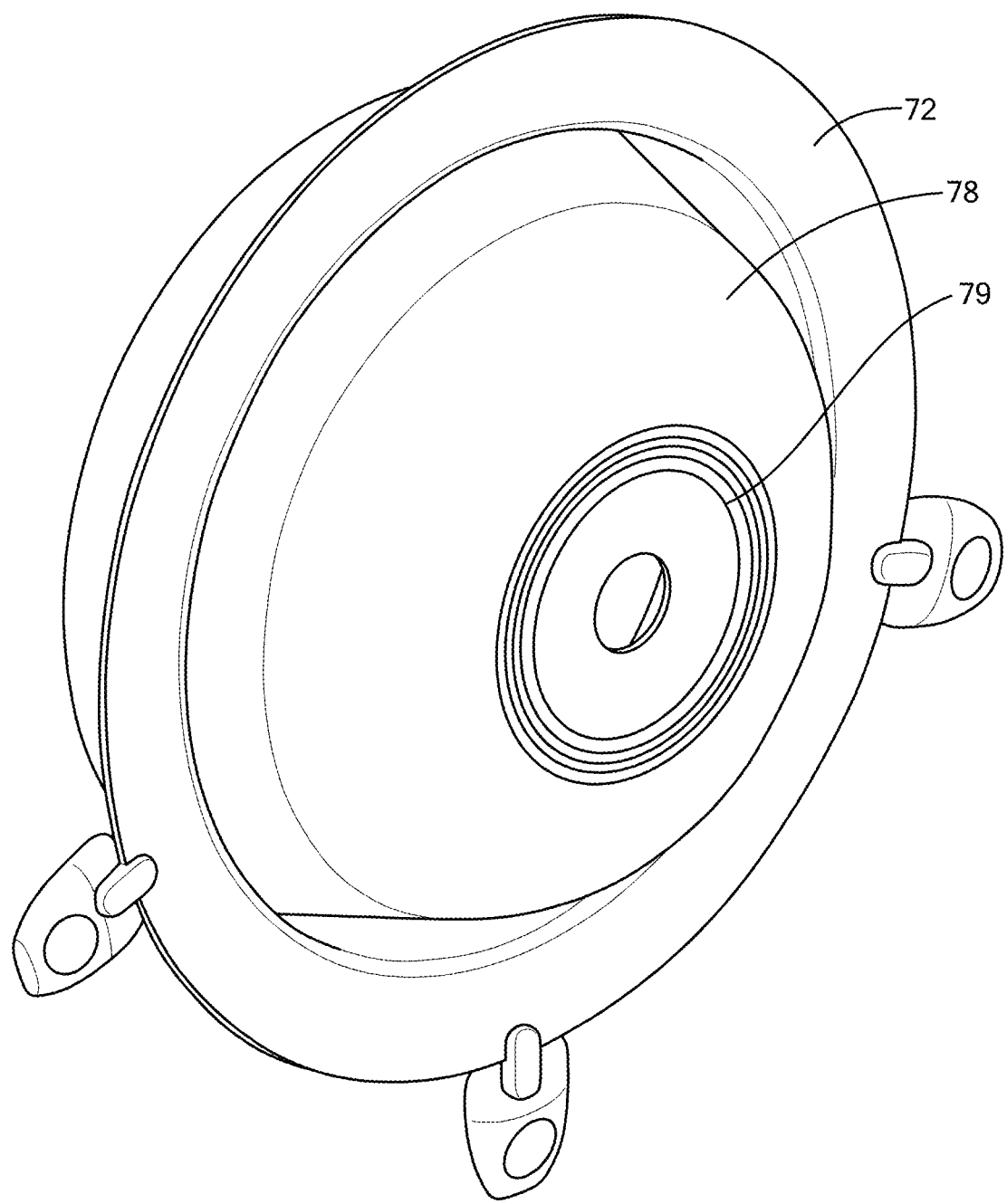
FIGS. 10-14 are schematic views showing how the patient drape terminal portion rotates relative to the reminder of the patient envelope portion.

In one version, shown in FIG. 8, retainers 80a, and 80b rotate with the gantry and relative to drape portions 72, 76 and 78. In one example, each retainer 80 includes member 90, FIG. 9 with a channel 92 for flexible spring member 74 of drape portion 72 and a roller 94 therein or some other feature such as a low friction slide or bearing surface. Sleeve 98, FIG. 8 on drape patient envelope 78 can be used to hold the drape fixed while the gantry and the stays rotate.

Figure 12:
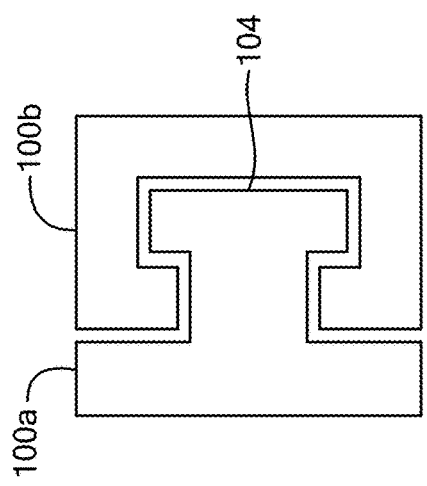
Figure 11:
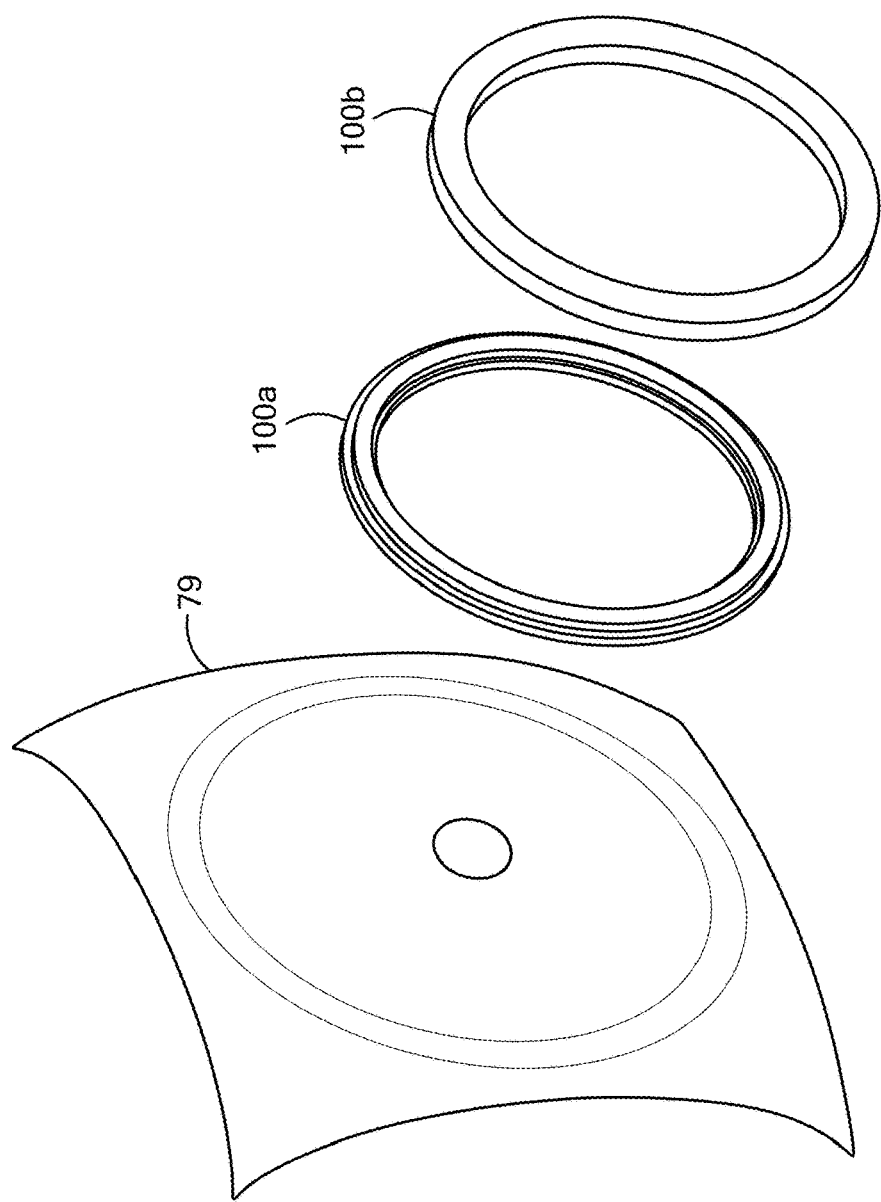
Figure 14:
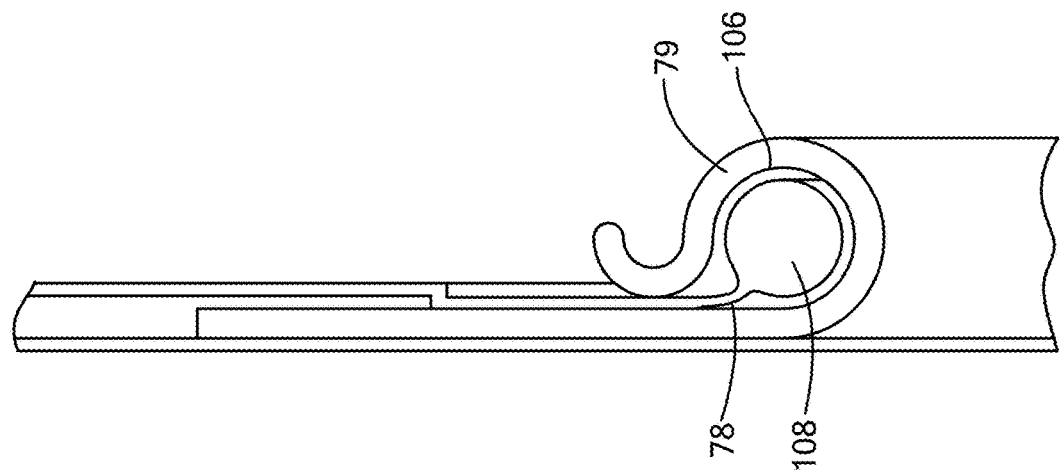
Figure 13:
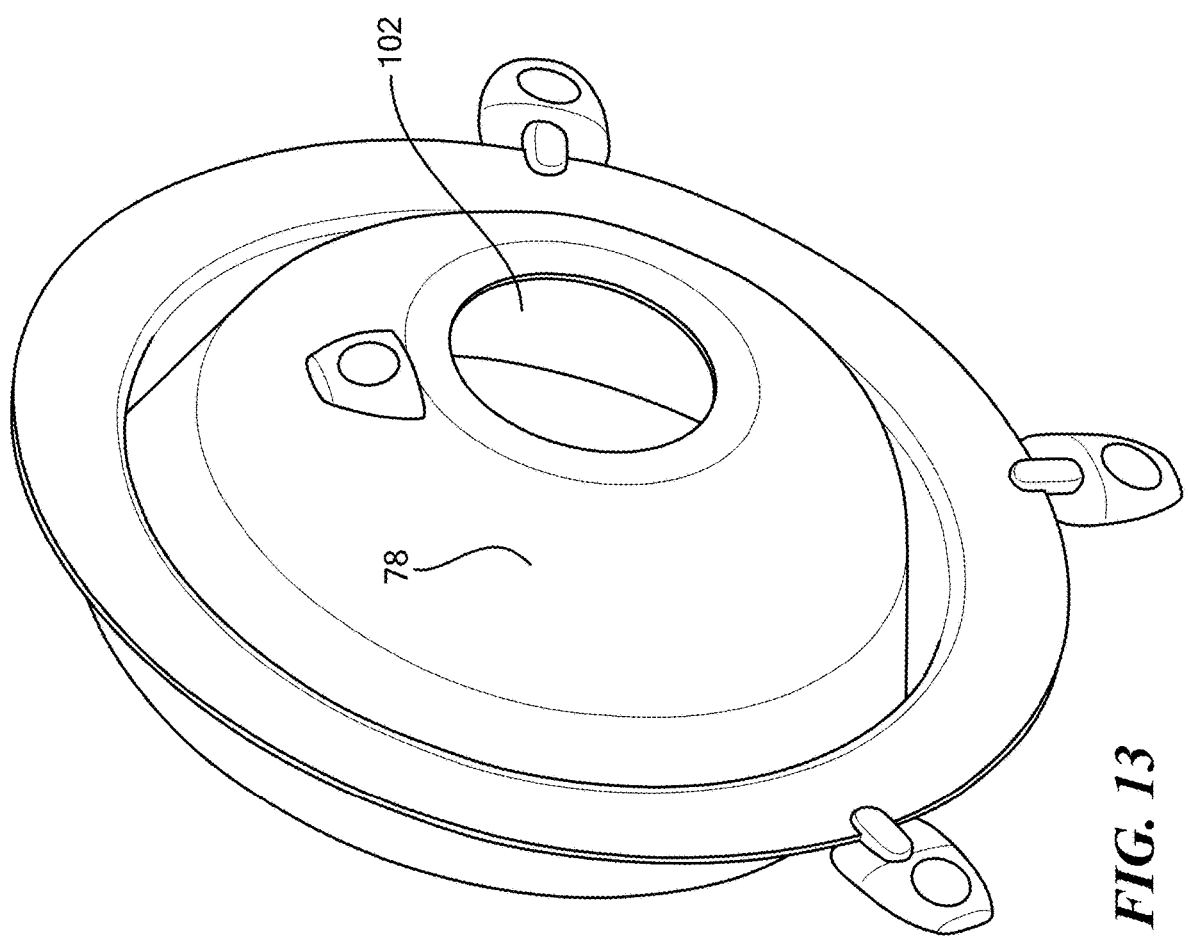
Figure 15:
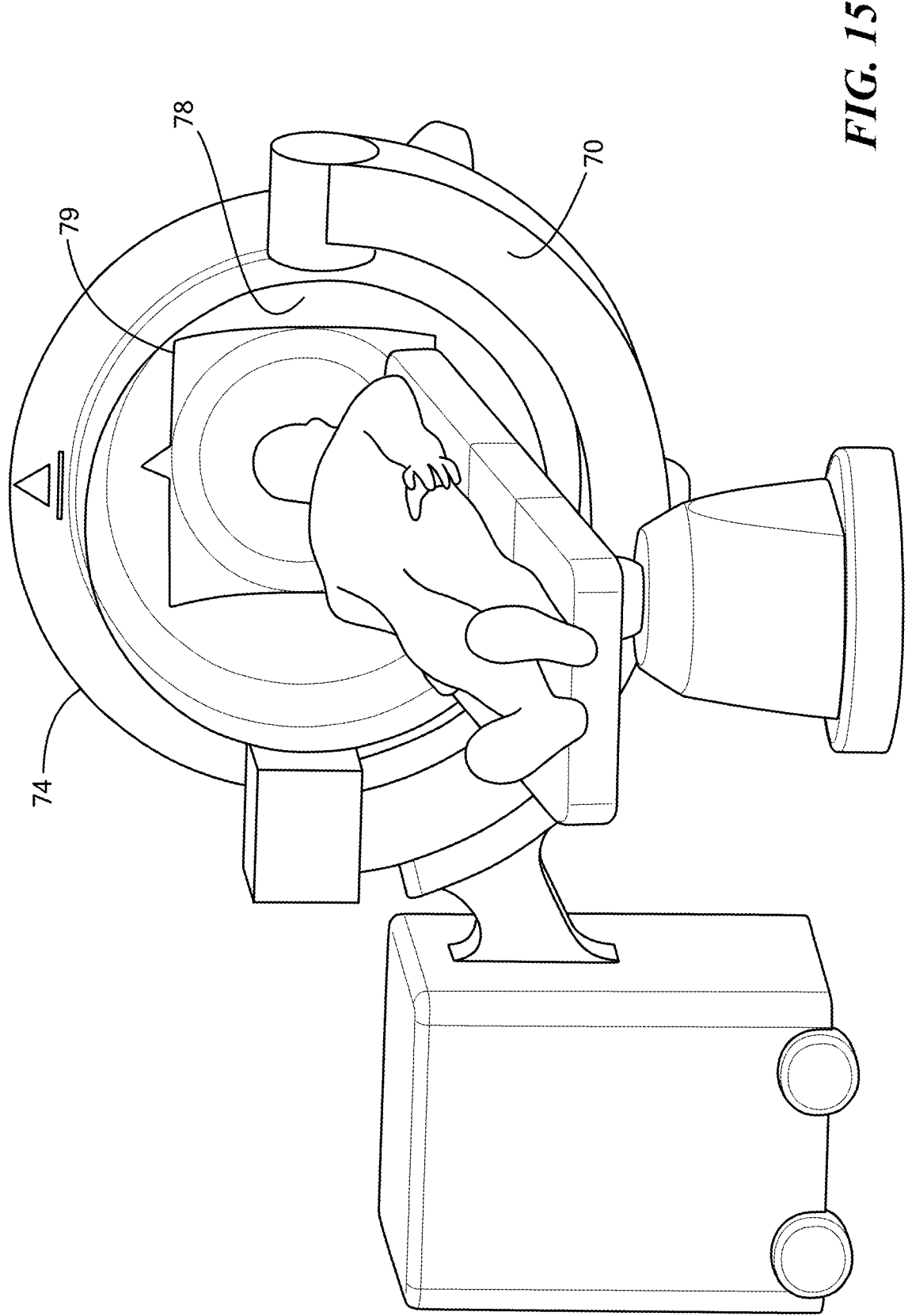
FIG. 15 is a schematic view showing the drape of FIG. 10 in position for a lateral scan.
Figure 16:
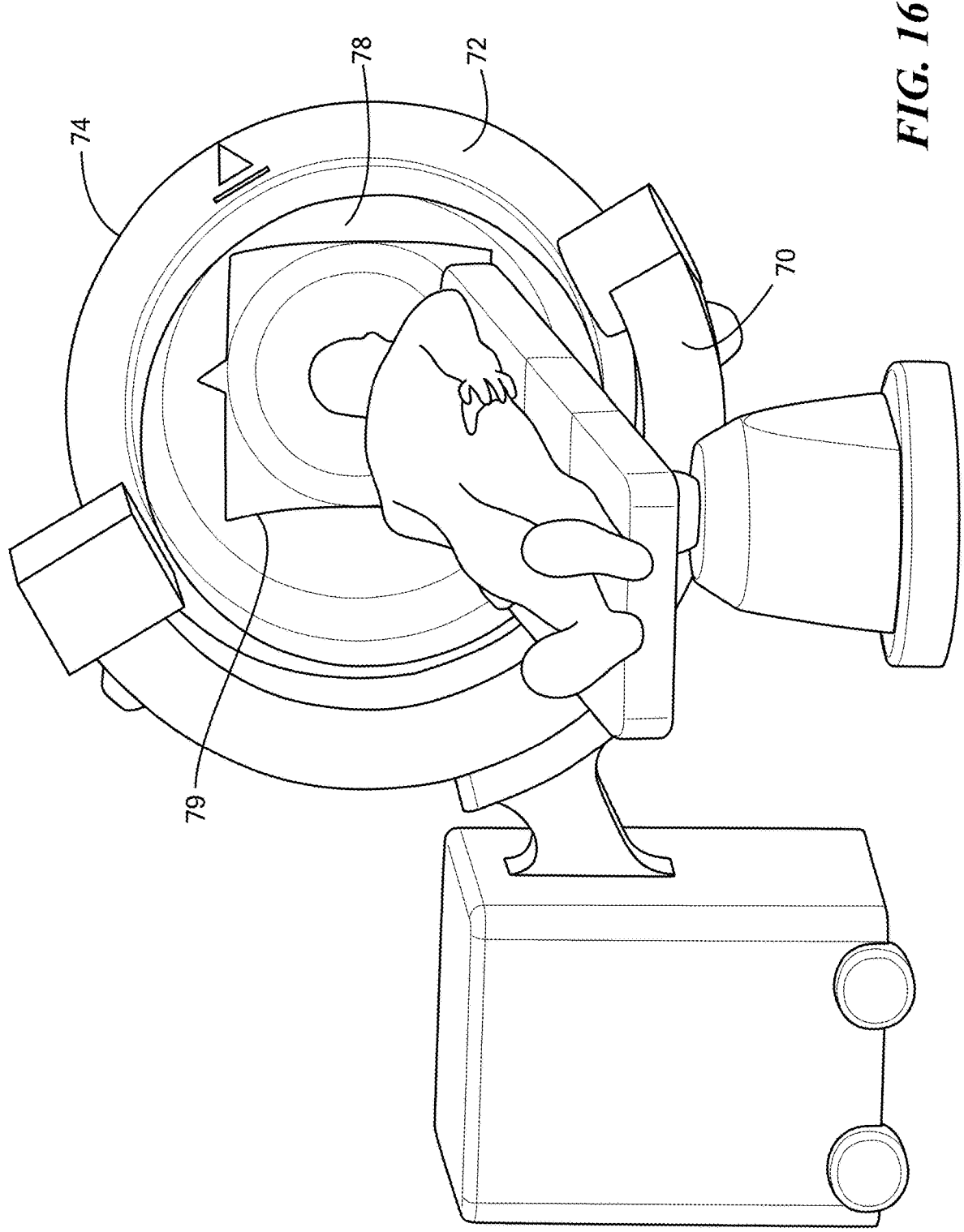
FIG. 16 is a schematic view showing the same drape in position for an oblique scan.
Figure 17:
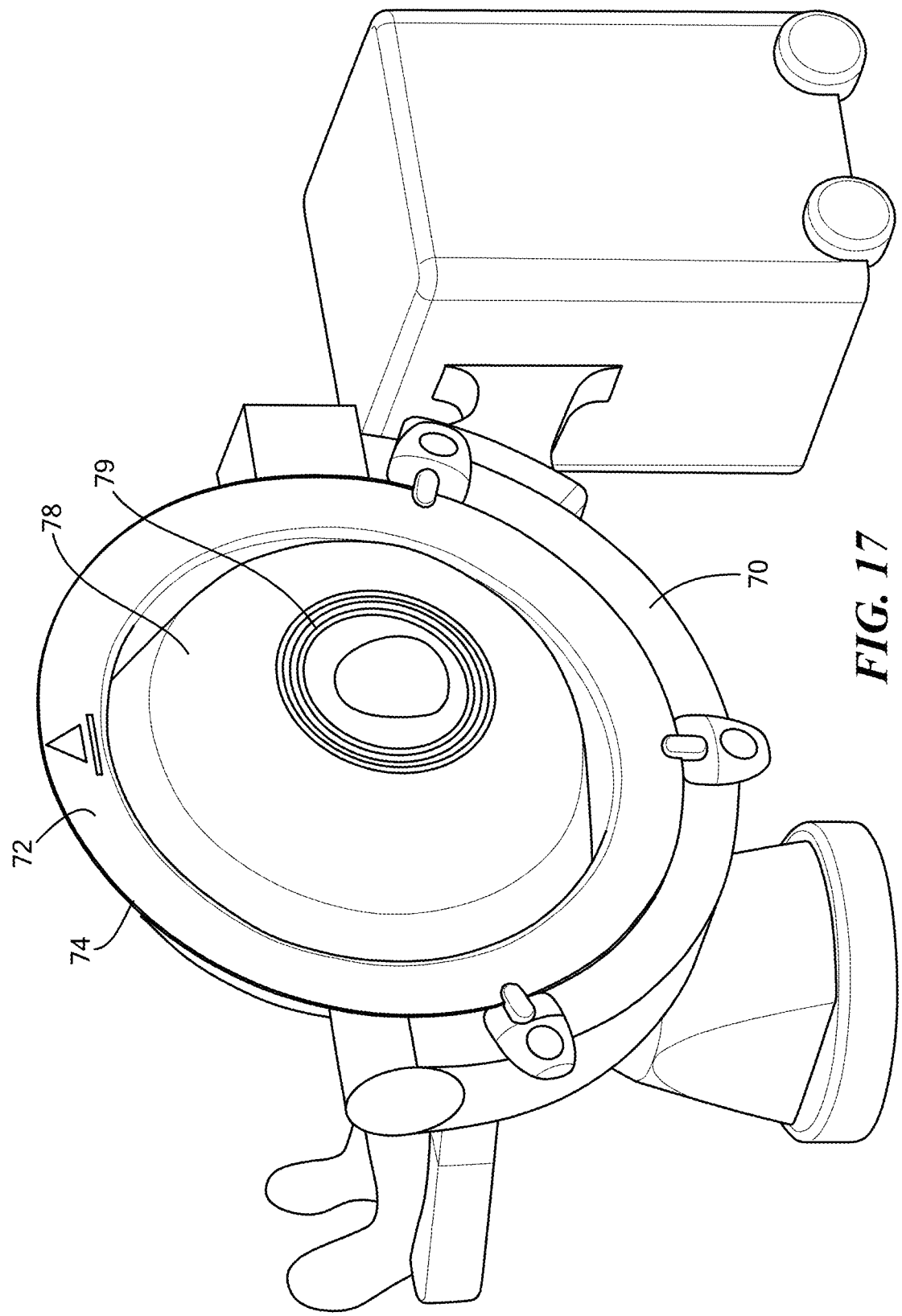
FIG. 17 is a schematic view showing the other side of the drape in position for a lateral scan.
Figure 18:
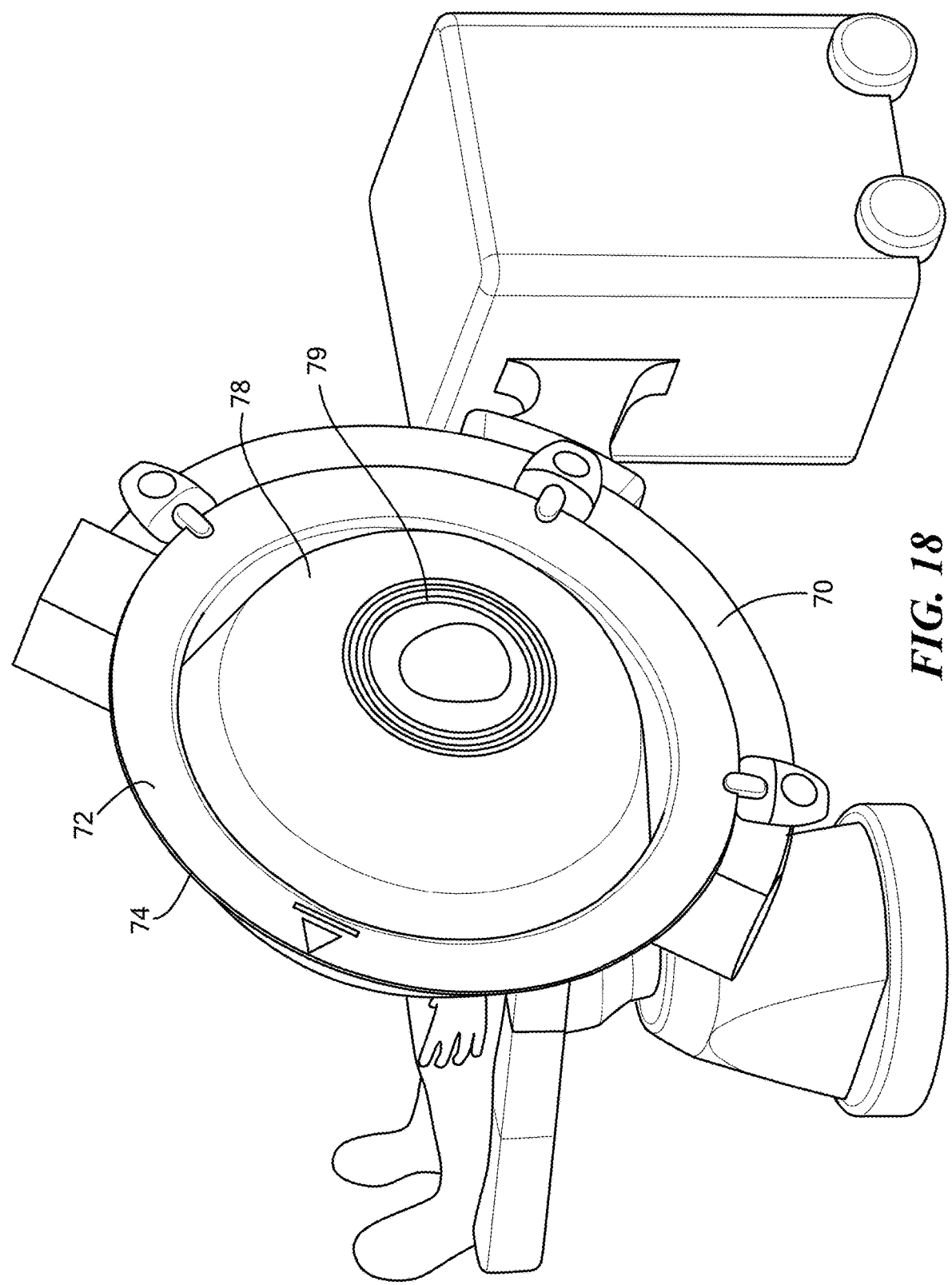
FIG. 18 is a schematic view of the other side of the drape in position for an oblique scan.
Figure 19:
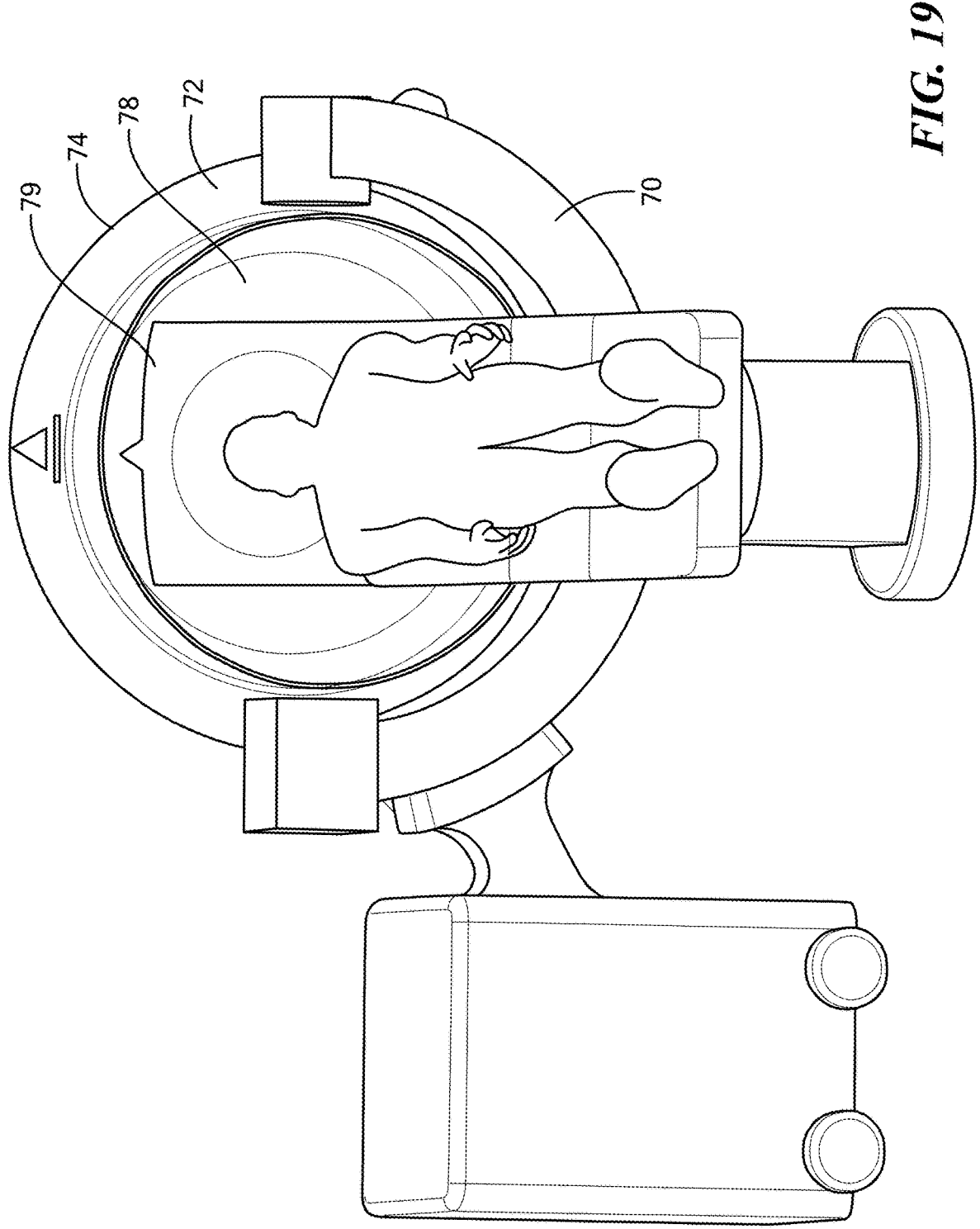
FIG. 19 is a schematic view showing the same drape in position for a scan when the patient is in the supine position.
Figure 20:
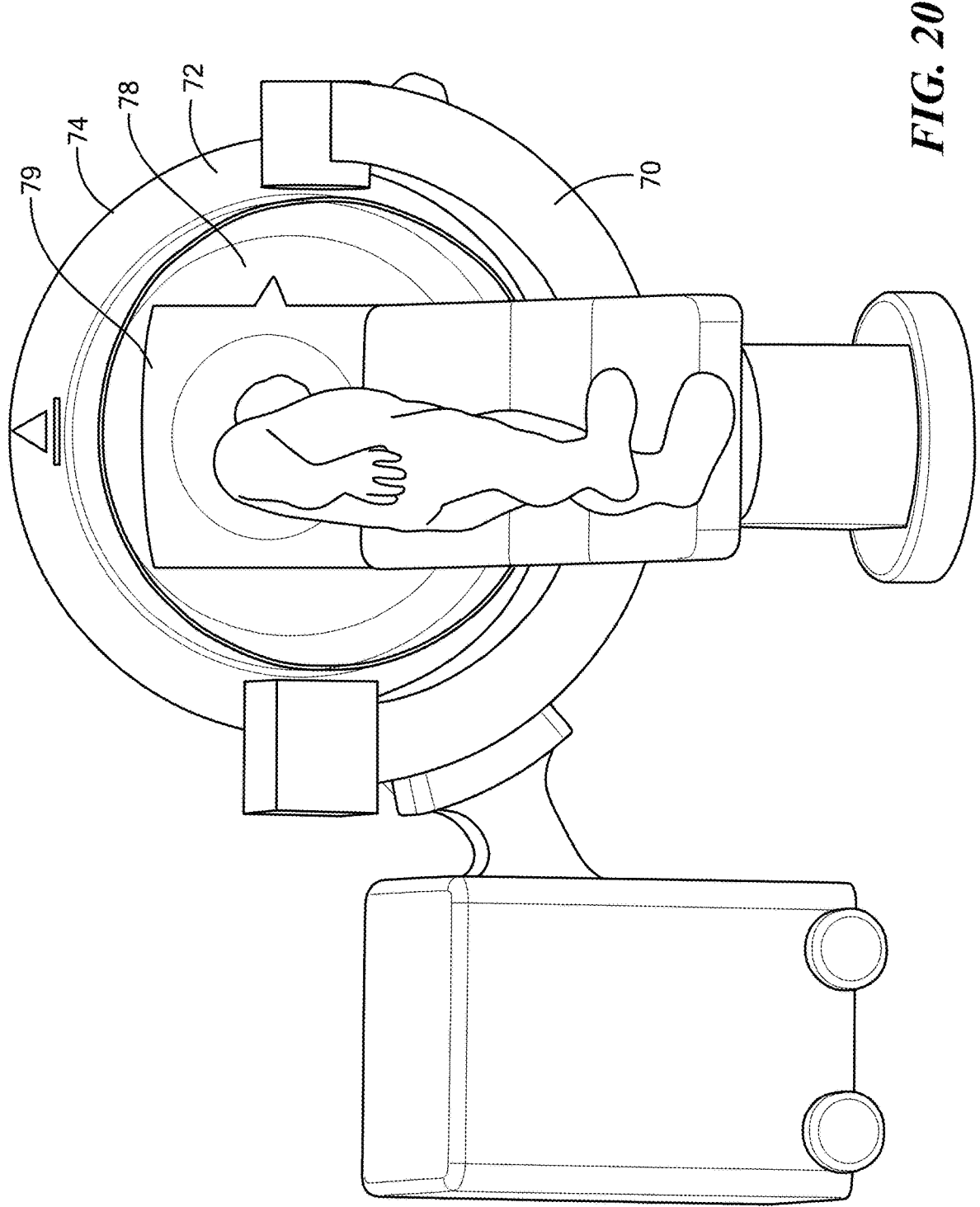
FIG. 20 is a schematic view showing the same drape in position for a patient rotated during surgery to a lateral position.

In another embodiment, the terminal portion 79 of the patient envelope portion 78 FIGS. 10-14 remains fixed and the remainder of the patient envelope portion 78 and gantry outer wall covering portion 72 rotate with the gantry. In one embodiment, ring 100a, FIGS. 11-13 is secured e.g., bonded, to terminal portion 79 and ring 100b is secured, e.g., bonded, to patient envelope portion 78 about the inside of opening 102 which surrounds terminal portion 79. Rings 100a and 100b include features which couple them together in a fashion such that ring 100b freely rotates with respect to ring 100a which stays fixed. For example, as shown in FIG. 12, ring 100b includes a track 104 and ring 100a includes a rail secured in track 104. FIG. 14 shows an embodiment where patient terminal portion 79 forms a track 106 for rail 108 associated with patient envelope drape portion 78. FIGS. 15-20 show the relative positions of the rotating and non-rotating drape portions during different scans of the patient.

Although specific features of the invention are shown in some drawings and not in others, this is for convenience only as each feature may be combined with any or all of the other features in accordance with the invention. The words "including", "comprising". "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. An imaging system gantry and patient drape comprising:
    a gantry first outer sidewall covering portion biased into a deployed shape and collapsible;
    a gantry inner wall covering portion extending inward of the gantry first outer sidewall covering portion;
    a patient envelope portion; and
    one or more stays extending from the gantry inner wall covering portion for securing to a gantry second outer side wall.

2. The drape of claim 1 in which the patient envelope portion extends from the gantry inner wall covering portion outwardly through the gantry.

3. The drape of claim 1 in which the patient envelope portion includes a patient fenestration.

4. The drape of claim 3 in which the fenestration is located at a terminal portion of the patient envelope portion.

5. The drape of claim 1 in which the patient envelope portion includes a stiffener forming a patient viewing window.

6. The drape of claim 1 in which the gantry first outer sidewall covering portion includes a flexible spring member.

7. The drape of claim 6 in which one portion of the drape rotates relative to another portion of the drape.

8. The drape of claim 7 in which the one or more stays rotate relative to the gantry first outer sidewall covering portion, the gantry inner wall covering portion and the patient envelope portion.

9. The drape of claim 8 in which the one or more stays include a channel for the flexible spring member.

10. The drape of claim 9 in which the channel includes a roller for the flexible spring member.

11. The drape of claim 7 in which one of said one portion of the drape and said another portion of the drape includes a track and the other of said one drape portion and said another portion of the drape includes a rail received in said track.

12. The drape of claim 11 in which there is a first ring secured to one said drape portion and a second ring secured to said other drape portion, said first ring including the track and the second ring including the rail.

13. The drape of claim 12 in which the first ring is secured to a terminal portion of the patent envelope portion and the second ring is secured to the patent envelope portion.

14. The drape of claim 1 further including retainers associated with the gantry first outer sidewall covering portion for attachment to the gantry.

15. An imaging system gantry and patient drape comprising:
    a gantry first outer sidewall covering portion biased into a deployed shape and collapsible via a flexible spring member;
    a gantry inner wall covering portion extending inward of the gantry first outer sidewall covering portion;
    a patient envelope portion;
    one or more retainers securing a portion of the drape to the gantry and including a channel for the flexible spring member; and
    one or more first drape portions rotating with the gantry and one or more second drape portions stationary with respect to rotation of the gantry.

16. The drape of claim 15 in which the channel includes a roller for the flexible spring member.

17. The drape of claim 15 further including a patient envelope terminal portion which is stationary and the one or more first drape portions which rotate with the gantry includes the first outer sidewall covering portion, the gantry inner wall covering portion, and the patient envelope portion.

18. The drape of claim 17 including a first ring secured to the patient envelope terminal portion and a second ring secured to the patient envelope portion and the second ring rotates with respect to the first ring.

19. The drape of claim 18 in which one said ring includes a track and the other said ring includes a rail received in the track.

* * * * *